(12) United States Patent
Lotfi (10) Patent No.: US 10,827,936 B2
(45) Date of Patent: Nov. 10, 2020

(54) SURFACE MODIFIED ELECTRODES

(71) Applicant: Advanced Bionics AG, Staefa (CH)

(72) Inventor: Atoosa Lotfi, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 1236 days.

(21) Appl. No.: 14/907,409

(22) PCT Filed: Aug. 15, 2013

(86) PCT No.: PCT/US2013/055102
§ 371 (c)(1),
(2) Date: Jan. 25, 2016

(87) PCT Pub. No.: WO2015/023280
PCT Pub. Date: Feb. 19, 2015

(65) Prior Publication Data
US 2016/0174860 A1 Jun. 23, 2016

(51) Int. Cl.
*A61B 5/04* (2006.01)
*A61N 1/05* (2006.01)
(Continued)

(52) U.S. Cl.
CPC ........ *A61B 5/04001* (2013.01); *A61N 1/0551* (2013.01); *B23K 26/352* (2015.10);
(Continued)

(58) Field of Classification Search
CPC .............. A61B 5/04001; A61N 1/0551; B23K 26/352; B23K 26/361–362;
(Continued)

(56) References Cited

U.S. PATENT DOCUMENTS 5,473,138 A * 12/1995 Singh .................. A61F 2/30771
219/121.69
5,683,443 A * 11/1997 Munshi .................... A61N 1/05
607/119
(Continued)

FOREIGN PATENT DOCUMENTS

WO 2013036988 3/2013

OTHER PUBLICATIONS

Green, et al. "Variation in Performance of Platinum Electrodes with Size and Surface Roughness," in Sensors and Materials, vol. 24, No. 4 (2012) 165-180. (Year: 2012).*
(Continued)

*Primary Examiner* — Lee S Cohen
*Assistant Examiner* — Erin M Cardinal
(74) *Attorney, Agent, or Firm* — Fabian Vancott (57) ABSTRACT

A method for forming an implantable electrode (100) includes exposing a conductive surface of the electrode (100) with a first application of an excimer laser (215) and creating a first surface texture on a conductive surface with a second application of the excimer laser. In one example, a low impedance implantable electrode includes a conductive surface and a coating disposed over the conductive surface. The coating may have a lower contact impedance with biological tissue than the conductive surface. At least a portion of the coating has an excimer laser textured surface.

20 Claims, 6 Drawing Sheets

(51) Int. Cl.
    B23K 26/354    (2014.01)
    B23K 26/40    (2014.01)
    B23K 26/361    (2014.01)
    B23K 26/352    (2014.01)
    B23K 26/362    (2014.01)
    B23K 101/34    (2006.01)
(52) U.S. Cl.
    CPC ........ *B23K 26/355* (2018.08); *B23K 26/3584* (2018.08); *B23K 26/361* (2015.10); *B23K 26/362* (2013.01); *B23K 26/40* (2013.01); *A61N 1/05* (2013.01); *B23K 2101/35* (2018.08)
(58) Field of Classification Search
    CPC .. B23K 26/3584; B23K 26/355; B23K 26/40; B23K 2101/35
    See application file for complete search history.

(56) References Cited

U.S. PATENT DOCUMENTS

| | | | |
|---|---|---|---|
| 5,800,500 | A | 9/1998 | Spelman et al. |
| 6,465,056 | B1 | 10/2002 | Chabrecek |
| 6,471,993 | B1 * | 10/2002 | Shastri ................. A61K 38/465 424/486 |
| 6,869,712 | B2 | 3/2005 | Mittelstadt et al. |
| 8,461,042 | B2 | 6/2013 | Dadd et al. |
| 2003/0170519 | A1 * | 9/2003 | Mittelstadt ............. C08J 5/2218 429/479 |
| 2003/0192784 | A1 * | 10/2003 | Zhou .................... A61N 1/0543 205/109 |
| 2005/0211680 | A1 * | 9/2005 | Li ......................... A61F 2/0077 219/121.68 |
| 2007/0265691 | A1 | 11/2007 | Swanson |
| 2011/0126410 | A1 | 6/2011 | Capcelea et al. |
| 2011/0127243 | A1 | 6/2011 | Pufulescu et al. |
| 2011/0130815 | A1 * | 6/2011 | Gibson ................ A61N 1/0541 607/116 |
| 2011/0270067 | A1 * | 11/2011 | Faraji ..................... H01L 24/83 600/377 |
| 2013/0085557 | A1 | 4/2013 | Terasawa |
| 2014/0357973 | A1 * | 12/2014 | Fisk ....................... A61B 5/042 600/372 |

OTHER PUBLICATIONS

Chikarakara "Laser Surface Modification of Biomedical Alloys" PhD dissertation, Dublin City University (2012) (Year: 2012).*
Thanawala et al., "Excimer laser fabrication of microbumps on platinum thin films," American Institute of Physics, Jul. 2007. Abstract Only, p. 1-2; DOI:http://dx.doi.org/10.1063/1.2760148.
Peach; LZH medical, industrial progress at Hannover Fair, Cochlear implant with external mic and speech processor "Laser technology can improve hearing", Apr. 25, 2012., pjs 1-4.

* cited by examiner

SURFACE MODIFIED ELECTRODES

BACKGROUND

Neural prosthetics can be used for electrical stimulation of neural tissue and sensing neural signals in the central and peripheral nervous systems. These neural prosthetics include one or more electrodes that make electrical contact with neural tissue. The charge transfer characteristics of the electrodes define how efficiently the electrodes can transfer or receive electrical signals from the neural tissue.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Neural prosthetics use electrodes to electrically stimulate neural tissue and sense electrical signals from the neural tissue. The charge transfer between the electrodes and neural tissue is in part determined by the electrochemistry of the electrode/tissue interface. To avoid energy losses and distortions of electrical signals, it can be advantageous for the electrical impedance of the interface to be small in the target stimulation/recording frequency range.

Transfer of charge within the neural prosthetic device and its electrodes is carried out by the flow of electrons. Within the biological environment, however, transfer of charge is typically carried out by the flow of ionic current between two or more electrodes. Therefore, to mediate the transition from electron flow in the electrode to ion flow in the biological environment and to minimize the impedance of the interface, the material, size, shape and topography of the electrodes can be carefully selected.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment. Features shown and/or described in connection with one figure may be combined with features shown and/or described in connection with other figures.

The absolute size and comparative sizes of objects illustrated in the figures is not necessarily to scale. The sizes of the objects have been illustrated to convey the principles described herein.

Figure 1:
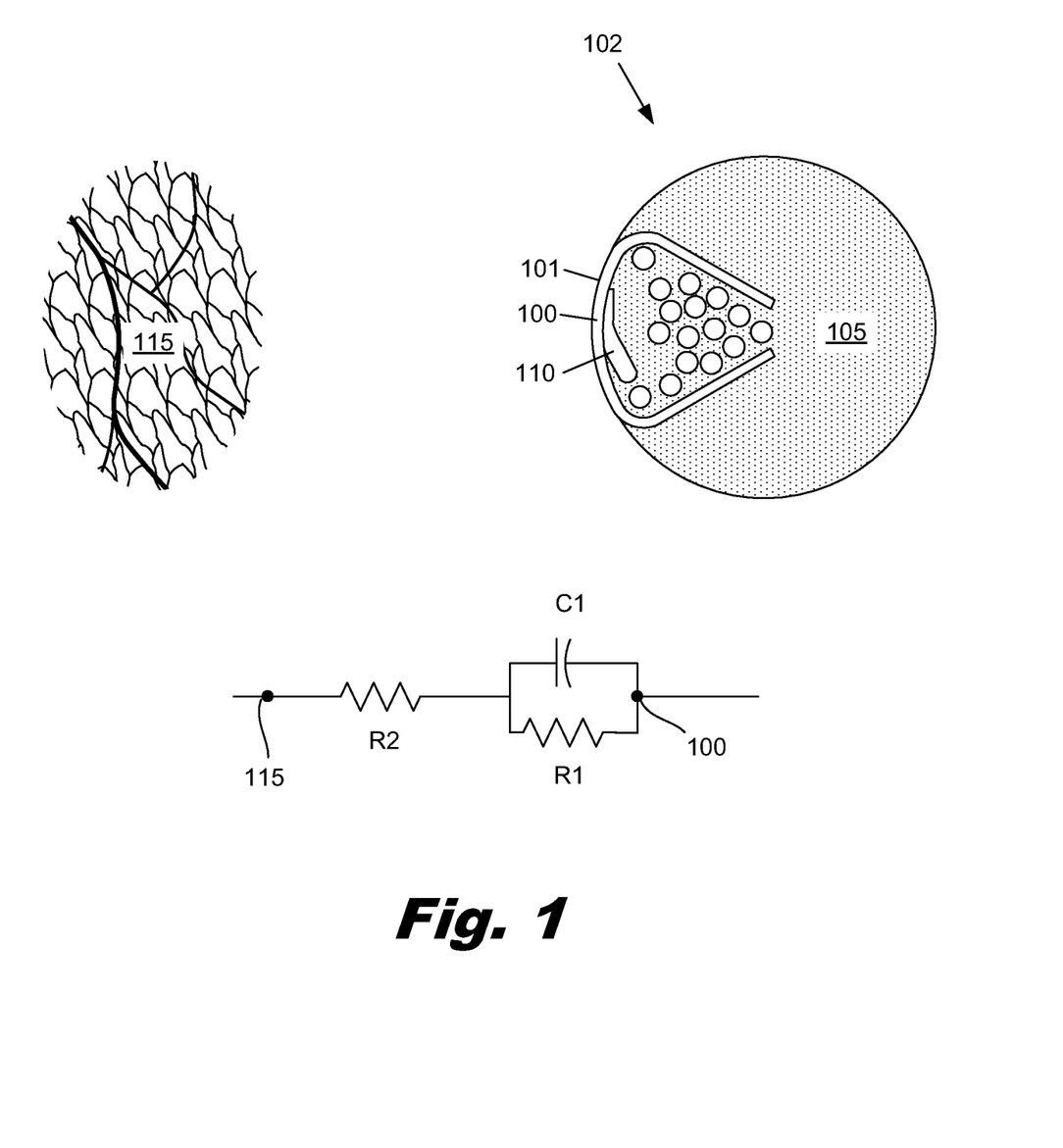
FIG. 1 is a cross sectional diagram of an electrode and target tissue with a corresponding electrical schematic, according to one example of principles described herein.

FIG. 1 is a diagram of a neural lead (102) that has been implanted in proximity to target biological tissue (115). The neural lead (102) may be any of a number of different leads, including a cochlear lead, a brain stimulation lead, an optical prosthesis, a spinal cord stimulator, a muscle stimulator, a sensor, or other type of neural lead. The neural lead (102) includes an electrode (100) with an exposed surface (101) that makes electrical contact with the surrounding biological tissue. The electrode (100) is electrically connected to a signal wire (110) and supported by an implant body (105). Ideally, electrical signals pass down the signal wire (110) to the electrode (100) and from the electrode (100) to the target biological tissue (115). For purposes of illustration, the electrode (100) is illustrated as being separated from the target biological tissue (115). For example, in a cochlear implant the electrode (100) may be separated from the target auditory nerve endings by the cochlear fluid and a wall of a cochlear duct. However, the principles described below apply to electrodes that are in direct contact with the target tissue as well as configurations that have intervening fluids and/or tissue between the electrode and target tissue.

A simplified electrical schematic of the interface between the electrode (100) and the target biological tissue (115) is shown below the cross sectional diagram. In the schematic, a first black circle on the right represents the electrode (100) and a second black circle on the left represents the target biological tissue (115). A first resistor R1 and a capacitor C1 represent the impedance at the surface of the electrode (100). The first resistance R1 and capacitance C1 can be dependent on a number of factors, including the exposed geometric surface area (GSA), the roughness of the electrode and the material that makes up the surface of electrode. For example, increasing the geometric size and/or active surface area of the electrode will increase its exposed surface area and its lower impedance.

The electrical resistance of the biological environment between the electrode (100) and the target biological tissue (115) is shown by a second resistance R2. The second resistance R2 can be dependent on a number of factors including the concentrations of ions and proteins in fluids, the type of intervening tissues, and the distance between the electrode and the target tissue.

The surface topology of the electrode can have significant effects on the performance of the system. For example, a rough electrode surface may have a greater active surface area in contact with biological tissues/fluids. This reduces the overall impedance at the electrode/tissue interface (R1 is significantly reduced while C1 is somewhat increased). However, electrode surfaces with very high aspect ratios may be prone to surface erosion. For example, peaks of the electrode surface may convey higher electrical currents to the surrounding tissues. These higher electrical currents may cause the peaks to dissolve into the biological tissue. This erosion can be undesirable for a number of reasons, including changes in the electrical characteristics of the electrode and contamination of the biological tissue.

The surface topology may also influence the biological response of the body to the implant. The initial response to the surgical implantation of the electrode is nonspecific adsorption of the proteins to the surface of the implant. As a result of the growth of the fibrous layer, impedance of the interface increases, with a corresponding increase in power consumption of the implanted device. The surface topology, including the pore size, structure spacing/height, and morphology of the electrode surface can influence adhesion of fibroblasts and other connective tissue to the electrode surface. The surface topology of the electrode surface can be designed to reduce fibrous tissue formation and reduce surface impedance over the lifetime of the electrode.

Figure 2:
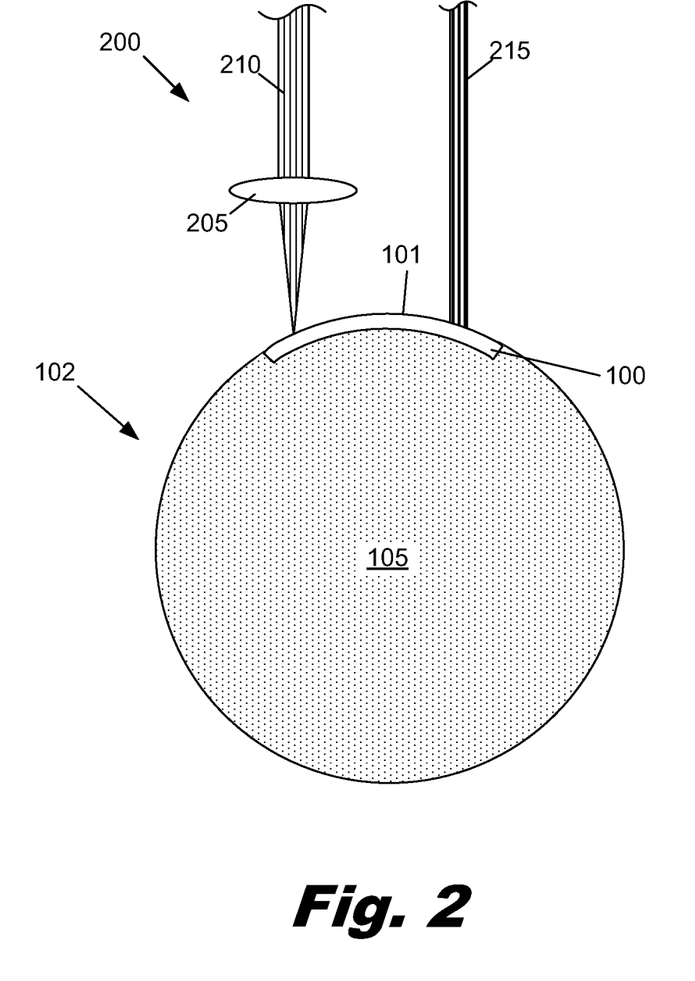
FIG. 2 is a diagram of laser modification of an electrode surface, according to one example of principles described herein.

FIG. 2 shows a cross sectional view of an implantable neural lead (102) that includes a body (105) and an electrode (100) with an exposed surface (101). The exposed surface (101) is in electrical contact with the surrounding biological tissues. The exposed surface (101) can be modified through application of laser energy.

On the left, a focusing laser system (200) is shown that uses a lens (205) or other technique to focus the laser beam (210) onto the exposed surface (101) of the electrode (100). This technique may have a number of advantages, including a small spot/feature size and precise location. However, because the exposed surface typically needs to be located at the focal point of the laser system, complex fixturing of both the laser and the electrode may be required. The use of a focusing laser system for modification of curved electrode surfaces can be even more challenging because the relative position and angle between the laser system and the electrode needs to be changed as the laser is scanned over the surface.

Excimer lasers are a form of ultraviolet laser that uses noble gasses, including noble gas halides. In ablative applications, the ultraviolet light from an excimer laser can add enough energy to disrupt the molecular bonds of a surface. This ablates the surface in a tightly controlled manner with almost no heating or change in the remainder of the material. At lower energy levels/pulse durations, the excimer laser can be used to produce localized melting rather than ablation.

An excimer laser (215) does not typically have tight focusing requirements and can be effectively used at a range of distances to modify an electrode surface (101). An excimer laser (215) may be used to modify an electrode surface (101) that has topography variations on the range of 10 to 100 microns. For example, a curved electrode surface (101) may have a center portion that is 50 microns higher than the edges of the electrode (100). The excimer laser (215) may be rastered across this surface without significant concern about the variation in height. If variations in the electrode surface (101) are greater than the tolerance of the excimer laser system, only coarse adjustments are necessary to bring it back into the acceptable range.

Figure 3:
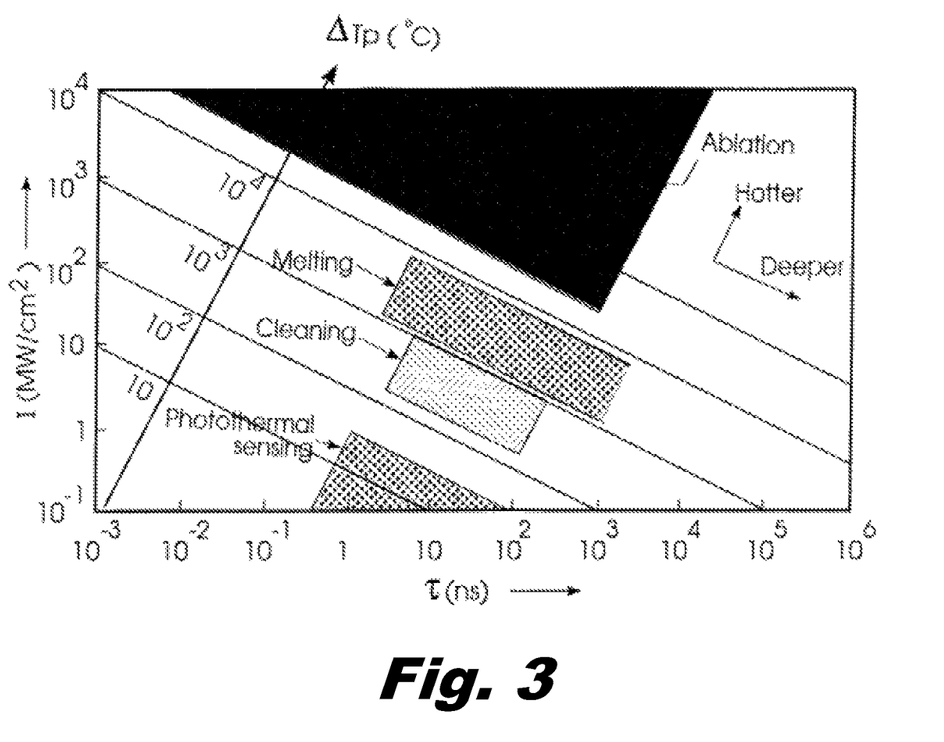
FIG. 3 is a graph of excimer laser performance for different pulse durations and intensities, according to one example of principles described herein.

FIG. 3 is a graph showing illustrative characteristics of an excimer laser (215, FIG. 2). The horizontal axis shows the duration of individual laser pulses in nanoseconds, with shorter pulses on the left and longer pulses on the right. The vertical axis shows intensity, in megawatts per centimeter square, with lower intensities on the bottom of the graph and higher intensities at the top of the graph. A third axis labeled ΔTp is at an angle to the vertical axis and shows the surface temperatures generated for a given pulse length and intensity. The temperatures are given in degrees Celsius. A number of boxes have been drawn to show the various effects on surfaces the excimer laser is applied to. For example, a shaded box labeled "Cleaning" is between 100 and 1,000 degrees Celsius with pulse durations of approximately one to hundreds of nanoseconds and intensities between approximately one and ten megawatts per centimeter square. A shaded box labeled "Melting" is between 1,000 and 10,000 degrees Celsius with pulse durations of approximately one nanosecond to hundreds of nanoseconds and intensities between approximately 1 and 100 megawatts per centimeter square. The portion labeled "Ablation" shows regions where the intensity and pulse durations produce localized temperatures exceeding 10,000 degrees.

Figure 4:
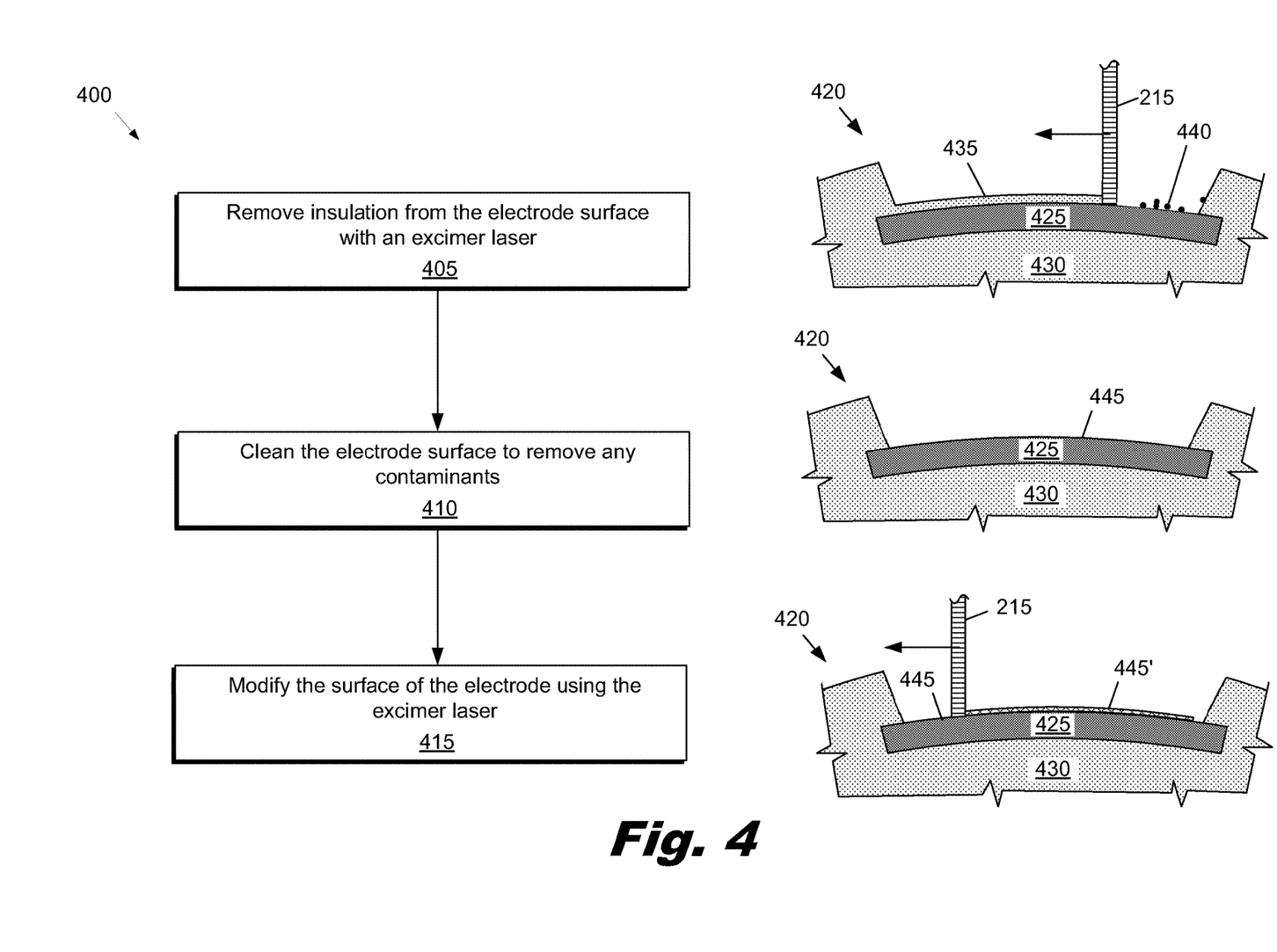
FIG. 4 is a flowchart of a method for surface modification of an electrode with corresponding illustrations, according to one example of principles described herein.

FIG. 4 shows one example of an illustrative method (400) for surface modification using an excimer laser (215). In this implementation, the lead (420) includes a recessed electrode (425) surrounded by an insulating body (430). The electrode (425) may be formed from platinum and joined to a silicone body (430). The electrode (425) may be placed in a mold and silicone may be injected around the electrode (425) and any wires or traces that are connected to the electrode (425). A layer of silicone (435) or other insulating material may be intentionally or unintentionally formed over the electrode (425). An excimer laser (215) may be used to remove all or a portion of the overlying silicone layer (435) (block 405). Unintentional deposition of silicone over the electrode surface is called "flash." Flash may be present in various thicknesses over electrode surfaces that were not completely seated against the mold. The parameters of the excimer laser system may be set to ablate the silicone flash with minimal disruption to the electrode surface itself.

In other situations, the conductive electrode surface may be intentionally covered with a thicker layer of silicone and an excimer laser (215) may be used to remove all or a portion of the silicone overlying the electrode surface. The removal of the overlying silicone layer (435) may result in particulates or other contaminants (440) being deposited on the electrode surface.

The electrode surface (445) is cleaned to remove any contaminants from the previous operation (block 410). For example, the electrode surface (445) may be cleaned using mechanical, chemical, or laser techniques. For example, the lead (420) may be placed in an ultrasonic bath with a specific solution and temperature for a predetermined period of time. In some examples, the electrode surface (445) may be cleaned through the application of additional laser energy. In other examples, the electrode surface (445) may be mechanically cleaned.

The electrode surface (445) is then modified to produce the desired surface texture (445') (block 415). For example, an excimer laser (215) may be used to ablate or melt the surface (445) of the electrode (425). Ablation of the electrode surface (445) can be used to roughen the surfaces by producing high aspect ratio features. Appropriate selection of laser pulse length, laser intensity, and location of the laser on the electrode surface can produce the desired surface roughness. The high aspect ratio features may cover all or only a portion of the exposed surface.

Figure 5:
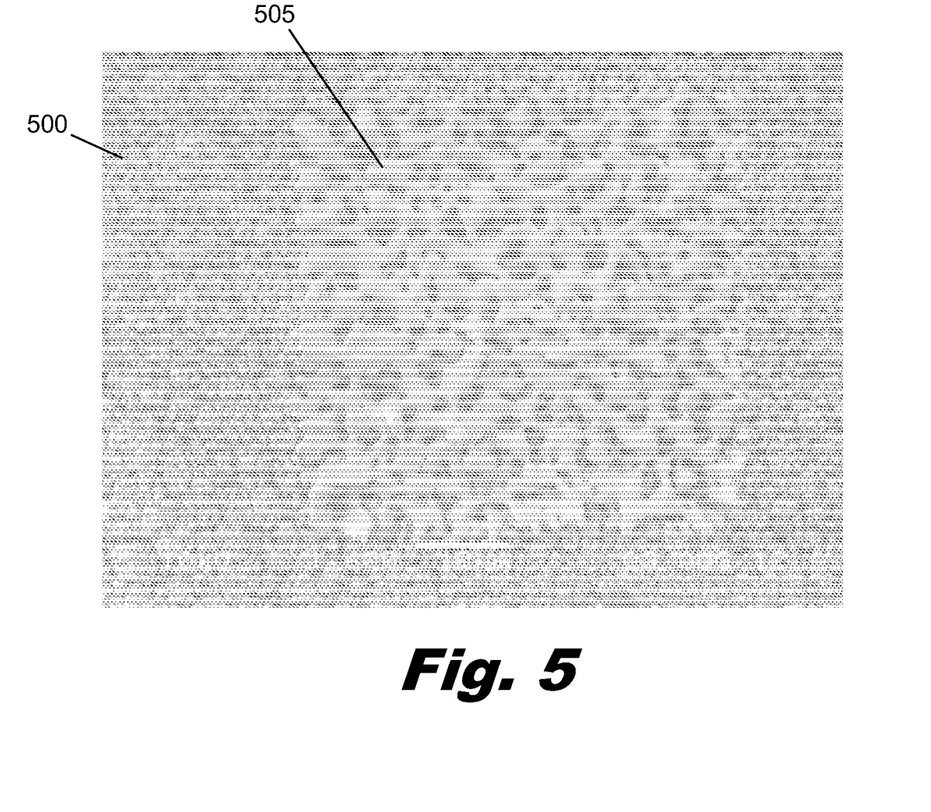
FIG. 5 is a scanning electron microscope image of an electroplated surface that has been modified through application of excimer laser energy, according to one example of principles described herein.

The method described above is only one example. A variety of other configurations could be used. The steps described above could be reordered, combined, omitted, or additional steps could be added. In one example, additional coatings could be added. FIG. 5 shows one example where an additional electroplated coating is added to the electrode surface and then subsequently modified through application of laser energy. In this example, the electrode surface was electroplated using techniques that specifically increase the surface roughness. The electroplating material (500) may be the same or different than the underlying electrode material. The electroplating may be performed before the electrodes are encapsulated or after the electrode surface has been cleaned.

Subsequent application of the excimer laser was used to melt and consolidate the peaks of the electroplated layer to form a modified surface (505). The modified surface (505) has larger surface features and smoother profiles than the original electroplated material (500). This reduces the tendency of the peaks to dissolve. Further, through selective application of the excimer laser, features with specific sizes and morphology can be formed. The sizes of the surface features can be selected to reduce adhesion of fibrous material to the electrode surface. As discussed above, adhesion of fibrous material to the electrode surface can increase the system impedance.

In other examples, the modification of the electrode surface using an excimer laser may be a two-step process. The excimer laser may be rastered over the electrode surface using high energy ablative settings to produce a high aspect ratio surface roughness. The high aspect surface roughness may cover all or only a portion of the exposed surface.

The excimer laser may then be rastered over the electrode surface using lower energy settings to melt/consolidate peaks on the surface. This may create a porous structure. The melted/consolidated areas may cover all or only a portion of the high aspect ratio surface roughness.

Figure 6:
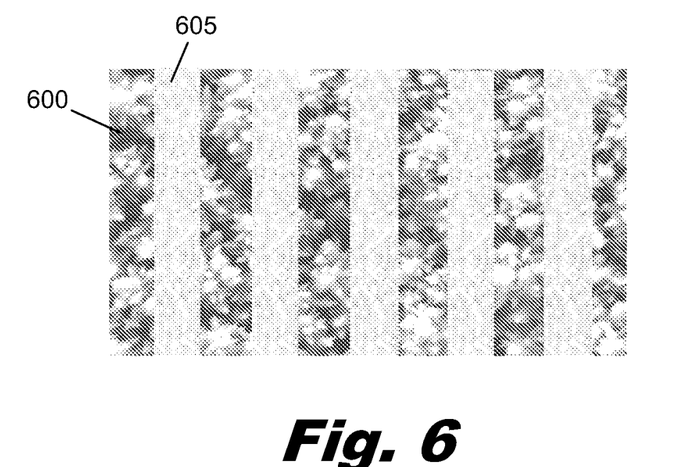
FIG. 6 is an illustration of an electrode surface modified through application of excimer laser energy to produce alternating texture stripes, according to one example of principles described herein.

FIG. 6 shows an illustration of an electrode surface that has been selectively modified using an excimer laser. The excimer laser has been used to consolidate a high aspect ratio surface (600) to produce alternating stripes of high aspect ratio surface and laser consolidated surface (605). This change in surface roughness may serve a variety of purposes, including decreasing dissolution of electrode material and decreasing fibrous adhesion to the electrode surface. Additionally, adding discontinuities in the electrode surface roughness may further reduce the impedance of the electrode. For example, the current density over the surface of the electrode increases at edges or other discontinuities. For a fixed electrode conductive area, an increase in the length of the edges or other discontinuities over the electrode surface can decrease impedance.

Figure 7A:
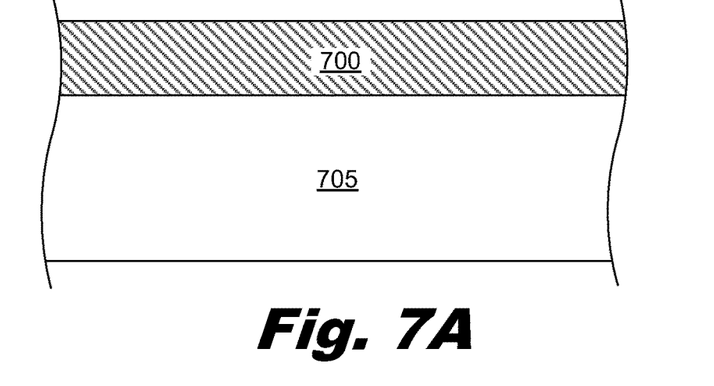
FIG. 7A is a cross sectional diagram of electrode with an impedance reducing coating, according to one example of principles described herein.
Figure 7B:
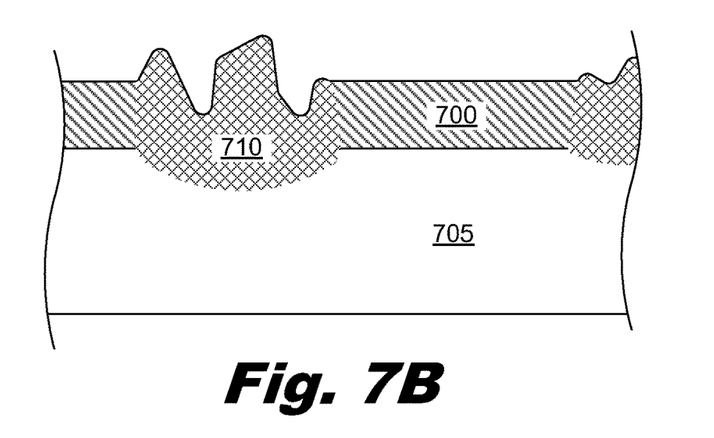
FIG. 7B is a cross sectional diagram of an electrode with an impedance reducing coating that has been secured through application of excimer laser energy, according to one example of principles described herein.
Figure 8:
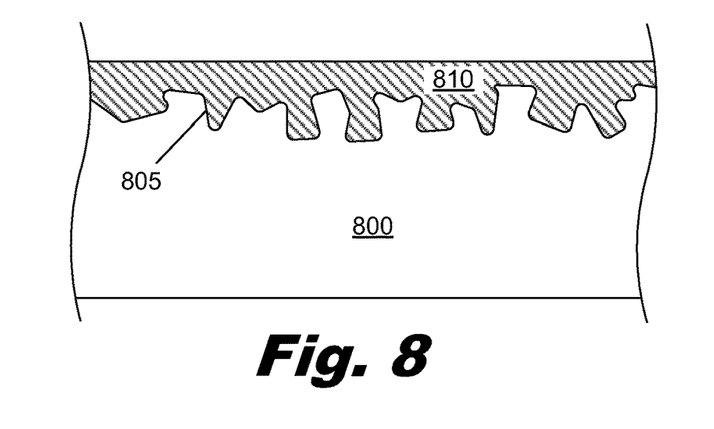
FIG. 8 is a cross sectional diagram of an electrode with laser modified surface and an impedance reducing overcoat deposited over the surface, according to one example of principles described herein.

In some examples, an additional impedance reducing coating may be formed over the electrode surface. FIGS. 7A, 7B, and 8 show various examples where an impedance reducing coating has been formed over the electrode surface. The impedance reducing coating may include platinum black, platinum gray, platinum/iridium alloys, dealloyed surfaces, conductive nanostructures or other materials. In one example, conductive polymers such as poly(3,4-ethylenedioxythiophene) (PEDOT) could be used in an impedance reducing coating. These impedance reducing coatings can be applied before or after the application of the excimer laser energy to modify the electrode surface. For example, the impedance reducing coatings may be applied before the surface is modified. The impedance reducing coatings may be applied in a number of ways, including electrochemical deposition, electrostatic deposition, printing, manual application, or other technique. For example, an ink containing platinum, iridium, or other conductive nanostructures may be printed onto the electrode surfaces using ink jet techniques.

Application of the excimer laser energy may then be used to improve adhesion of the coating to the surface by partially melting portions of the electrode/impedance reducing coating. FIG. 7A shows an impedance reducing coating (700) disposed over the electrode (705). FIG. 7B shows the same impedance reducing coating (700) and electrode (705) with selected portions that have been modified using an excimer laser. The laser modified portions (710) have melted and combined the impedance reducing coating (700) and the underlying electrode material. The laser modified portions (710) may or may not cover the entire surface of the electrode (705). By selectively applying laser energy, the impedance reducing coating (700) is more securely attached to the underlying electrode (705). Further, the laser modified portions (710) may increase the surface area of the electrode (705) and decrease adhesion of fibrous tissue to the electrode surface.

Additionally or alternatively, the impedance reducing coating (700) may be applied after the application of the laser energy. FIG. 8 shows one example of an electrode (800) with an excimer laser modified surface (805) and an impedance reducing overcoat (810). For example, if a two-step laser process is used to create a high surface roughness and then consolidate the peaks, there may be significant overhangs, cavities and other features. When the impedance reducing coating (810) is formed on this excimer laser modified surface (805), the coating (810) can extend into these features to mechanically lock the coating (810) in place.

In sum, the new techniques and structures described above maximize the charge transfer of the electrode surface over the lifetime of an implant without significantly impacting the manufacturability of the electrode arrays. The laser modification of the surface can be applied to the electrode surface itself or to a surface that is deposited over the electrode. The surface modification increases the electrochemical surface area of an electrode. Where an impedance reducing overcoat is used, the overcoat may have a charge transfer capability that is greater than that of the electrode surface. Surface modification of the electrode may also help impedance reducing coatings to more securely attach to the electrode. Further, the modified surface may have feature sizes and distribution that inhibit adhesion and growth of biological tissues on the surface. By lowering the impedance at the surface of the electrode and ensuring that the impedance remains low throughout the lifetime of the implant, the power consumption of the device can be significantly reduced. Lower power consumption and longer battery life will provide possibility for new system architectures such as fully implantable cochlear systems.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A low impedance implantable electrode comprising:
a conductive surface;
a coating disposed over the conductive surface, the coating comprising a lower contact impedance with biological tissue than the conductive surface; and
a laser textured surface on at least a portion of the coating, wherein the conductive surface and the coating have melted and combined in the laser textured surface portion of the coating of the electrode.

2. The electrode of claim 1, wherein the laser textured surface is an excimer laser textured surface.

3. The electrode of claim 1, wherein the coating is a printed coating.

4. The electrode of claim 1, wherein the coating is an electroplated coating.

5. The electrode of claim 1, wherein the laser textured surface of the coating has increased surface area compared to the non-laser textured surface of the coating.

6. The electrode of claim 1, wherein the laser textured surface of the coating has larger surface features, smoother profiles, and reduced peak dissolution compared to the non-laser textured surface of the coating.

7. A method for forming an implantable electrode comprising:
electroplating a conductive surface to create an electroplated surface having a first surface texture with a high aspect ratio roughness; and
applying a laser to form an alloy between the electroplated surface and the conductive surface to form the implantable electrode.

8. The method of claim 7, wherein the first surface texture covers less than all of the conductive surface.

9. The method of claim 7, wherein applying the laser reduces the roughness to produce a second surface texture having reduced peak dissolution.

10. The method of claim 9, wherein applying the laser comprises rastering the laser over the first surface texture to restructure peaks of the first surface texture.

11. The method of claim 9, wherein the second surface texture covers less than all of the first surface texture.

12. The method of claim 7, wherein the conductive surface and the electroplated surface each comprise a noble metal.

13. The method of claim 12, wherein the electroplated surface comprises platinum and the conductive surface comprises platinum.

14. The method of claim 7, wherein the laser is an excimer laser.

15. A method for forming a low impedance implantable electrode comprising:
disposing an impedance reducing coating over a conductive surface, and
applying a laser to melt and combine a portion of the coating and the conductive surface to form the low impedance implantable electrode.

16. The method of claim 15, wherein the impedance reducing coating comprises at least one of: platinum black, platinum gray, a platinum iridium alloy, and iridium.

17. The method of claim 15, wherein disposing the impedance reducing coating over the conductive surface comprises printing platinum ink over the conductive surface.

18. The method of claim 15, wherein the laser is an excimer laser.

19. The method of claim 15, wherein applying the laser increases the surface area of the electrode.

20. The method of claim 15, wherein applying the laser melts and consolidates peaks of the coating to form a modified surface having larger surface features, smoother profiles, and reduced peak dissolution.

* * * * *